United States Patent [19]

Kubokawa

[11] Patent Number: 4,593,680
[45] Date of Patent: Jun. 10, 1986

[54] ENDOSCOPE

[75] Inventor: Hiroaki Kubokawa, Tokyo, Japan

[73] Assignee: Olympus Optical Co., Ltd., Tokyo, Japan

[21] Appl. No.: 678,336

[22] Filed: Dec. 5, 1984

[30] Foreign Application Priority Data

Jan. 17, 1984 [JP] Japan .................................. 59-4710

[51] Int. Cl.$^4$ .............................................. A61B 1/00
[52] U.S. Cl. ...................................................... 128/4
[58] Field of Search ........................ 128/4, 5, 6, 7, 3; 350/96.26

[56] References Cited

U.S. PATENT DOCUMENTS

| | | | |
|---|---|---|---|
| 3,561,432 | 2/1971 | Yamaki et al. .......................... | 128/6 |
| 3,924,608 | 12/1975 | Mitsui ................................... | 128/6 X |
| 3,960,143 | 6/1976 | Terada ................................... | 128/4 |
| 4,452,236 | 6/1984 | Utsugi ................................... | 128/4 |

FOREIGN PATENT DOCUMENTS 59-34239  2/1984  Japan .

Primary Examiner—William H. Grieb
Attorney, Agent, or Firm—Frishauf, Holtz, Goodman & Woodward

[57] ABSTRACT

An endoscope has a flexible insertion section extending from an operation section. A chamber is formed in the extended end of the insertion section to open externally, and a guide channel extends from the chamber to an inlet formed at the operation section through the insertion section. A guide member is movably arranged in the chamber. One end of a wire is coupled to the guide member, and the member is rotated by pushing or pulling the wire. When a treating unit is introduced into the chamber through the inlet and the guide channel, the guide member guides the end portion of the treating unit in a predetermined direction. The chamber has a side wall for guiding the member, and the member has a side wall opposite to the side wall. A friction reducing member is fixed to the side wall and contact with the side wall of the chamber so as to reduce the friction between the side walls.

16 Claims, 9 Drawing Figures

ENDOSCOPE

BACKGROUND OF THE INVENTION

The present invention relates to an endoscope and, more particularly, to an endoscope having a guide member for guiding a treating unit such as catheter or forceps.

An endoscope has in general an operation section, a slender insertion section extending from the operation section, and a connection section. Recently, an endoscope having a treating unit guide member at the end structure of an insertion section has been proposed to guide the end of a treating unit, such as a catheter or forceps, introduced to the end of the insertion section through a channel for the treating unit. In this endoscope, the guide member is rotatably provided by a supporting shaft in a chamber formed at the end of the insertion section. An operating wire is connected at one end thereof to the guide member through a rotary ring in the guide member. The wire extends to the operation section through the insertion section. The leading direction of the treating unit may be altered by pulling or pushing the wire to rotate the guide member.

The end of the insertion section is very small, the installing space of the guide member is restricted, and the supporting shaft for supporting the guide member must be short. Thus, the engaging length of the guide member with the supporting shaft is very short, and when the guide member is rotating by pulling the wire, a powerful twisting force acts upon the guide member in addition to the rotary force around the supporting shaft. The guide member rubs against the side walls of the chamber for operating as the guide of the guide member. Consequently, the guide member increases its resistance in the rotating mode, and an operator can feel a lull in the operating force of the guide member. Moreover, this resistance decreases the operability of the endoscope. Further, there arise defects, i.e., the wire stretches, the wire is removed from the guide member, or a guide pipe for the wire is bent.

SUMMARY OF THE INVENTION

The present invention has been made in consideration of this and has for its object to provide an endoscope capable of improving the operability of a treating unit guide member for guiding a treating unit such as catheter or forceps.

In order to achieve the above object, there is provided, according to the present invention, an endoscope comprising friction reducing means, provided on at least one of a side wall of a guide member and a side wall of a chamber opposite to the side wall of the guide member, for reducing the friction between the side walls of the chamber and the guide member, thereby reducing the frictional resistance of the guide member in the moving mode.

BRIEF DESCRIPTION OF THE DRAWINGS

FIGS. 1 to 5 show an endoscope according to an embodiment of the present invention, wherein FIG. 1 is a perspective view showing the entire endoscope, FIG. 2 is an enlarged perspective view showing a distal end portion of an insertion section, FIG. 3 is a perspective view of a friction reducing member and a treating unit guide member, FIG. 4 is a sectional view taken along the line III—III of FIG. 2, and FIG. 5 is a sectional view taken along the line IV—IV of FIG. 2;

DETAILED DESCRIPTION OF THE PREFERRED EMBODIMENTS

Embodiments of the present invention will now be described in detail with reference to the accompanying drawings.

Figure 1:
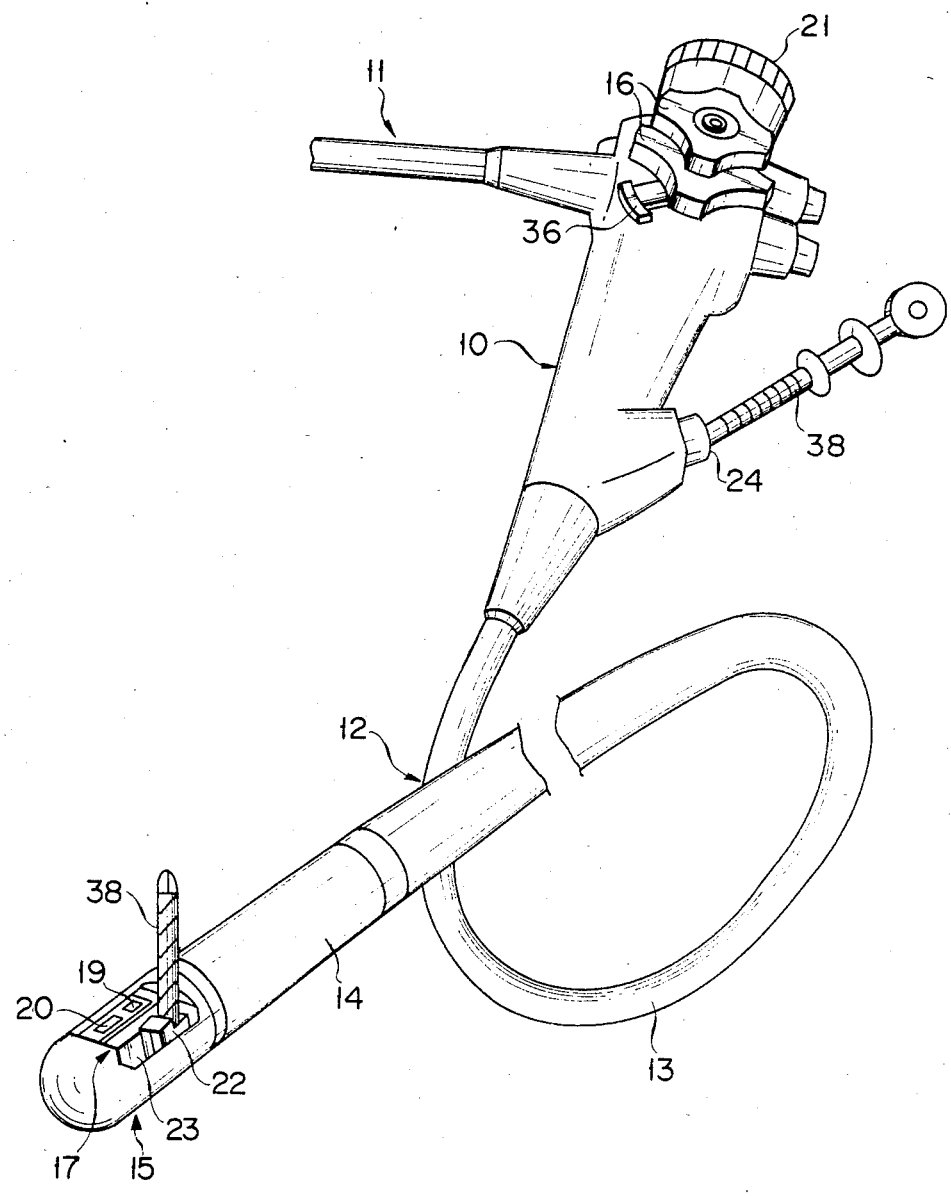
Figure 2:
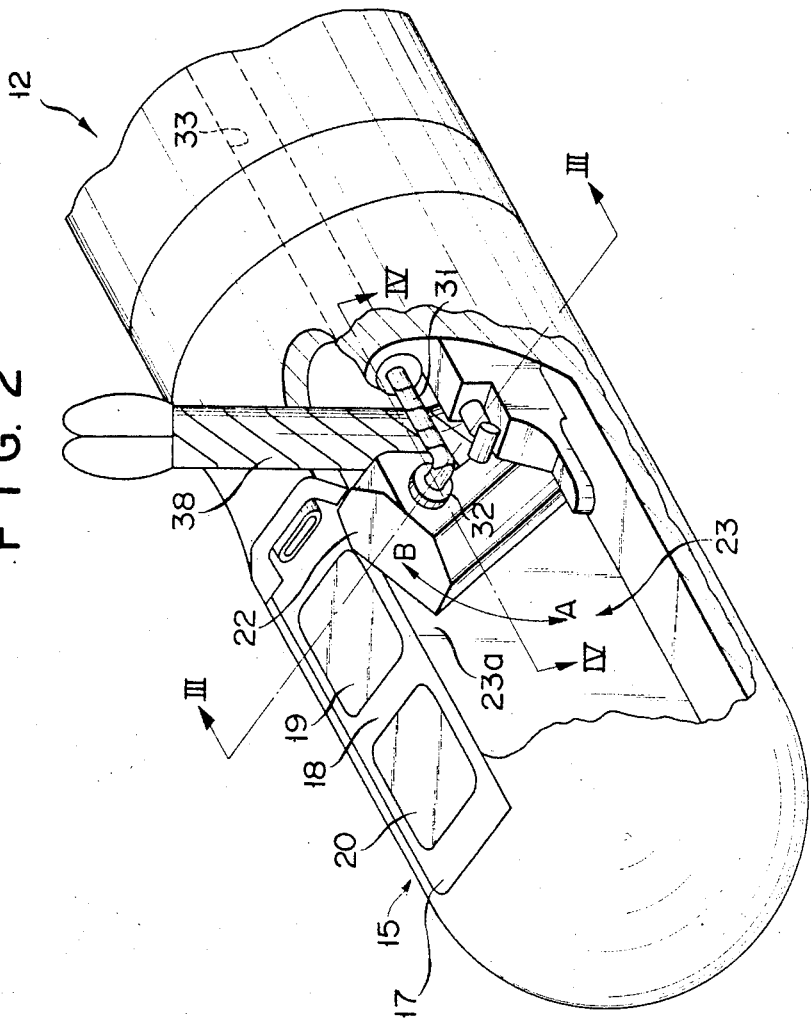
Figure 3:
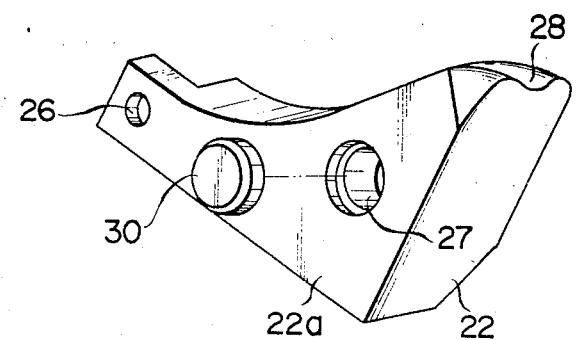
Figure 4:
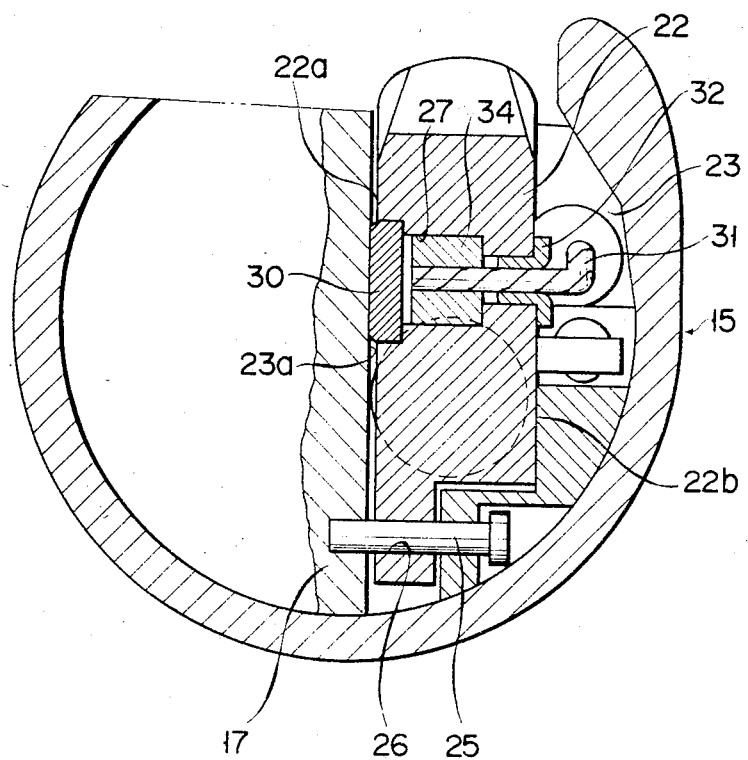

As shown in FIG. 1, an endoscope comprises an operation section 10, a slender insertion section 12 extending from the section 10, and a connection section 11 extending from the section 10 and coupled to a light source (not shown). The section 12 has a flexible portion 13, a bendable portion 14 and an end structure 15. The portion 14 can be remotely bent by an angle adjusting knob 16 provided on the section 10. As shown in FIGS. 1 and 2, an end body 17 is provided in the end structure 15, and an observation window 19 and an illumination window 20 are formed on the side wall 18 of the body 17. The window 19 is optically coupled to an eyepiece 21 of the operation section 10 through an image transmitting optical system (not shown) mounted in the insertion section 12. Further, a chamber 23 for containing a treating unit guide member 22 (to be described in detail) is formed in the body 17, and the chamber 23 is opened at the side wall 18 of the body 17. The chamber 23 communicates with a forceps port 24 formed in the section 10 through a channel 33 extending in the insertion section 12.

As shown in FIGS. 2 to 5, the treating unit guide member 22 is arranged in the chamber 23. The guide member 22 is rotatably supported by a rotational shaft 25 installed between the side walls of the chamber 23, and disposed in the vicinity of the outlet of the channel 33. As better understood from FIGS. 3 and 4, the member 22 has a side wall 22a opposite the side wall 23a of the chamber 23 and a side wall 22b opposite the side wall 22a. At the member 22 are formed a supporting hole 26, through which the shaft 25 is inserted, and a mounting hole 27 having an axis parallel to the hole 26. These holes 26 and 27 are respectively opened at the side walls 22a and 22b. A guide slot 28 for guiding a treating unit is formed on the upper surface of the member 22. A friction reducing member 30 made, for example, of an ethylene tetrafluoride resin chip is attached to the end of the hole 27 at the side of the wall 22a. The member 30 is slightly projected from the wall 22a of the member 22 and in contact with the wall 23a of the chamber 23. An operating wire 31 is attached to the wall 22b of the member 22. More particularly, one end of the wire 31 is inserted into the hole 27 through a rotary ring 32 mounted on the end of the hole 27 at the side of the wall 22b, and further fastened to a lock ring 34 engaged within the hole 27. This ring 34 is fastened by swaging to the wire 31. However, when an adhesive such as ceramics is coated on the ring 34 before swaging and then swaged, the locking effect of the ring 34 to the wire 31 is further enhanced. The wire 31 is connected through a wire guide channel (not shown) extending through the insertion section 12 to a forceps erecting knob 36 (FIG. 1) mounted on the operation section 10.

The operation of an endoscope constructed as described above will now be described. The treating unit such as forceps 38 is first inserted from the port 24 of the section 10, and the end of the forceps is projected through the channel 3 into the chamber 23. In this case, the wire 31 is telescoped back and forth by operating the knob 36 of the section 10 to tilt the guide member 22 toward a direction of an arrow A in FIG. 2 so that the forceps 38 readily projects into the chamber 23. Thus, the end portion of the forceps 38 projects into the chamber 23 under the guidance of the slot 28 of the member 22. Subsequently, the knob 36 is operated to rotate the member 22 toward a direction of an arrow B in FIG. 2, thereby directing the end of the forceps 38 in the desired direction. When the guide member 22 is rotated around the shaft 25, the reducing member 30 slides on the wall 23a of the chamber 23.

According to the endoscope constructed as described above, the following advantages can be provided.

Figure 5:
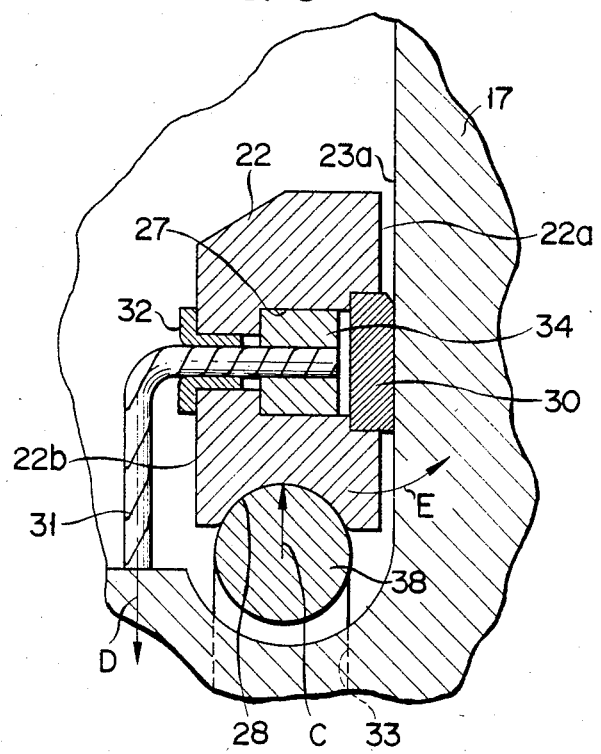

A twisting force E acts on the member 22 by reaction C from the forceps 38 and tension force D of the wire 31, as shown in FIG. 5, when the wire 31 is telescoped back and forth to rotate the member 22. Thus, the wall 22a of the member 22 is pressed toward the wall 23a of the chamber 23. However, in this embodiment described above, the member 30 projects from the wall 22a of the member 22. Therefore, only the member 30 slides on the wall 23a of the chamber 23. Consequently, the slide resistance of the member 22 is remarkably decreased, thereby reducing the operating force of the member 22. As a result, the operability of the knob 36 can be improved, and defects such as the extension of the wire 31, the removal of the wire from the ring 32, or the damage of the guide channel can be prevented.

Figure 6:
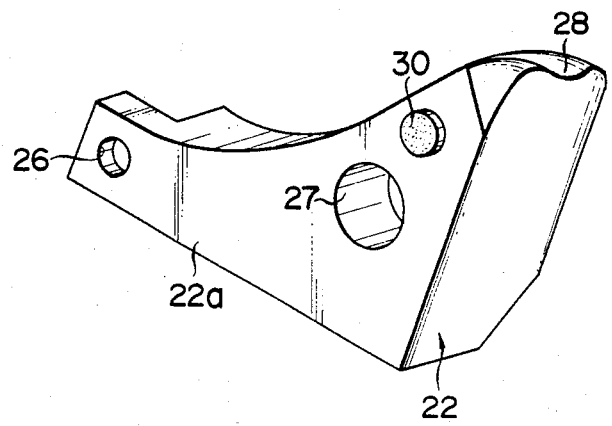
FIGS. 6 to 8 are perspective views of modified embodiments of the friction reducing member.

The present invention is not limited to the particular embodiment as described above. Various changes and modifications may be made within the spirit and scope of the present invention. For example, though the reducing member 30 is fastened to the end of the hole 27 of the member 22 in the above embodiment, the member 30 may be mounted at the position displaced from the hole 27 to the side of the slot 28 on the wall 22a of the member 22 as shown in FIG. 6. Further, though not shown, the member 30 may be fastened to the wall 23a of the chamber 23 and in contact with the wall 22a of the member 22. Moreover, the member 30 may be fixed to the wall 22b of the member 22 and in contact with a wall of the chamber 23.

Figure 7:
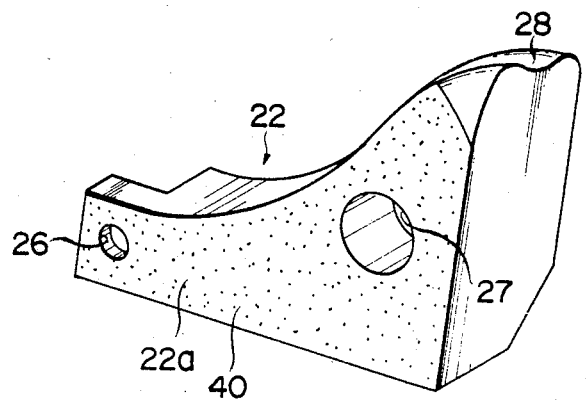
Figure 8:
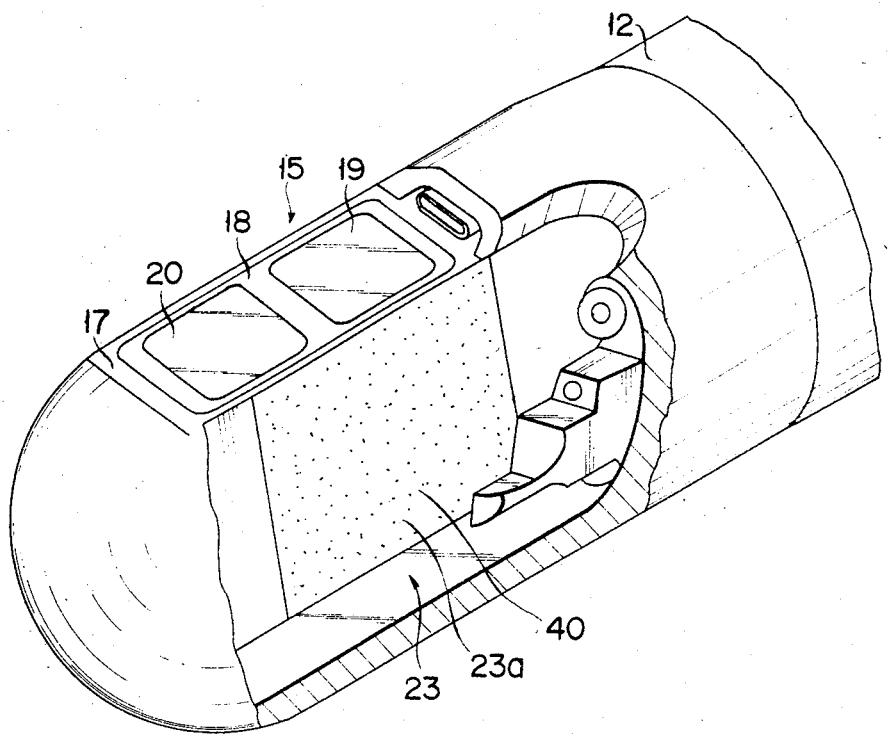

In the embodiment described above, the friction reducing member 30 as friction reducing means is mounted on the side wall of the guide member or on the side wall of the chamber. However, instead of the member 30, a friction reducing layer 40 made, for example, of ethylene tetrafluoride resin or polyacetal resin may be coated on both the side wall 22a of the member 22 or the side wall 23a of the chamber 23, as shown in FIGS. 7 and 8. Further, the member 30 and the layer 40 may be associated in combination. Moreover, the above embodiment shows an endoscope of the side-viewing type. However, the present invention may also be applied to an endoscope of the direct-viewing type or the inclined-viewing type.

In the first embodiment described above, the treating unit guide member 22 is exemplified as rotatable. The present invention is not limited to that particular embodiment. For example, the guide member may be formed as shown in a second embodiment shown in FIG. 9. In this embodiment, a treating unit guide member 22 is slidably arranged in a chamber 23 formed at the end portion 15 of an insertion section 12. Then, a friction reducing means such as a friction reducing layer 40 is formed on at least one of the side wall 22a of the member 22 and the side wall (not shown) of the chamber opposed to the side wall 22a.

Figure 9:
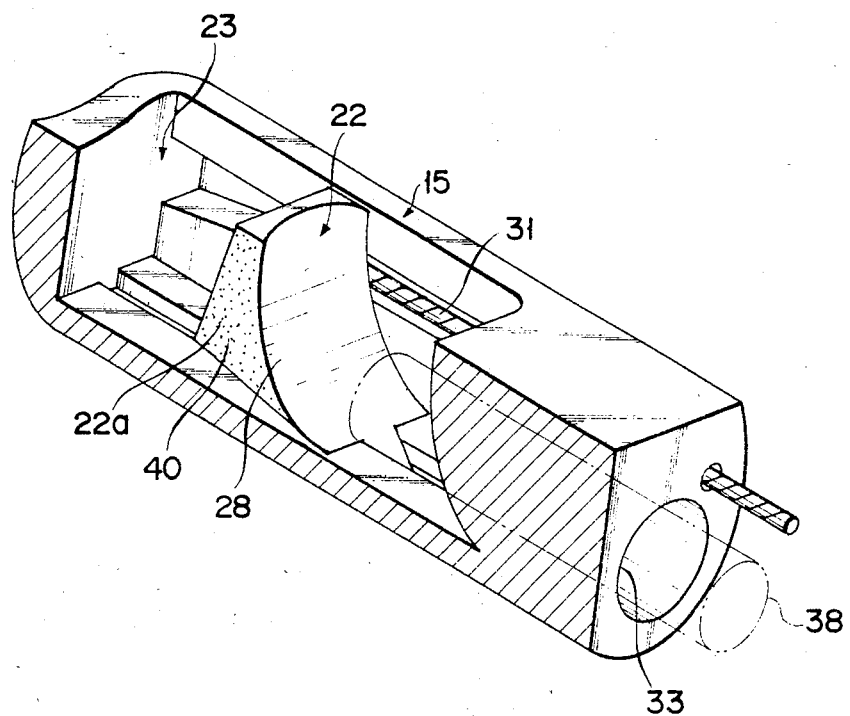
FIG. 9 is an enlarged perspective view showing an essential part of an endoscope according to a second embodiment of the present invention.

The same advantages as those of the first embodiment can be provided even in the second embodiment constructed and described above. In FIG. 9, the same reference numerals as in FIGS. 1 to 5 denote the same parts in the first embodiment, and the detailed description thereof will be omitted.

What is claimed is:

1. An endoscope comprising:
   an operation section having an inlet for a treating unit;
   a flexible insertion section extending from the operation section, said insertion section having a chamber formed in the extended end thereof and opened externally, and a guide channel extending from the inlet to the chamber through the insertion section;
   a guide member, movably arranged in said chamber, for guiding the end portion of the treating unit, introduced into the chamber through the inlet and the guide channel, in a predetermined direction, said chamber having a side wall for guiding the movement of said guide member and said guide member having one side wall opposite to the side wall of the chamber and another side wall opposite to said one side wall;
   operation means, having one end coupled to said another side wall of the guide member and extending to the operation section through the insertion section, for operating the guide member from the operation section; and
   friction reducing means for reducing the friction between the side walls of the guide member and the chamber, said friction reducing means including a friction reducing layer coated on the side wall of the guide member and being in contact with the side wall of the chamber.

2. An endoscope according to claim 1, wherein said friction reducing layer is formed of ethylene tetrafluoride resin.

3. An endoscope according to claim 1, wherein said friction reducing means includes a friction reducing layer coated on the side wall of said chamber and being in contact with one side wall of said guide member.

4. An endoscope according to claim 3, wherein said friction reducing layer is formed of ethylene tetrafluoride resin.

5. An endoscope accordng to claim 3, wherein said friction reducing layer is formed of polyacetal resin.

6. An endoscope according to claim 3, wherein said friction reducing layer is formed of polyacetal resin.

7. An endoscope according to claim 1, wherein said guide member is rotatably provided in said chamber.

8. An endoscope according to claim 1, wherein said guide member is slidably arranged in said chamber.

9. An endoscope comprising:
   an operation section having an inlet for a treating unit;
   a flexible insertion section extending from the operation section, said insertion section having a chamber formed in the extended end thereof and opened externally, and a guide channel extending from the inlet to the chamber through the insertion section;
   a guide member, movably arranged in said chamber, for guiding the end portion of the treating unit, introduced into the chamber through the inlet and the guide channel, in a predetermined direction, said chamber having a side wall for guiding the movement of said guide member and said guide member having one side wall opposite to the side wall of the chamber and another side wall opposite to said one side wall;

operation means, having one end coupled to said another side wall of the guide member and extending to the operation section through the insertion section, for operating the guide member from the operation section; and friction reducing means for reducing the friction between the side walls of the guide member and the chamber, said friction reducing means including a friction reducing member projecting from said side wall of the guide member and being in contact with the side wall of the chamber.

10. An endoscope according to claim 9, wherein said friction reducing member is formed of ethylene tetrafluoride resin.

11. An endoscope according to claim 9, wherein said friction reducing member is formed of polyacetal resin.

12. An endoscope according to claim 9, wherein said friction reducing means includes a friction reducing layer coated on the side wall of said chamber and being in contact with the side wall of said guide member.

13. An endoscope according to claim 12, wherein said friction reducing layer is formed of ethylene tetrafluoride resin.

14. An endoscope according to claim 12, wherein said friction reducing layer is formed of polyacetal resin.

15. An endoscope according to claim 9, wherein said guide member is rotatably provided in said chamber.

16. An endoscope according to claim 9, wherein said guide member is slidably arranged in said chamber.

* * * * *